United States Patent [19]

Sharkawy

[11] Patent Number: 5,021,044

[45] Date of Patent: Jun. 4, 1991

[54] CATHETER FOR EVEN DISTRIBUTION OF THERAPEUTIC FLUIDS

[75] Inventor: Ahmed Sharkawy, College Station, Tex.

[73] Assignee: Advanced Cardiovascular Systems, Inc., Santa Clara, Calif.

[21] Appl. No.: 304,062

[22] Filed: Jan. 30, 1989

[51] Int. Cl.⁵ .......................................... A61M 31/00
[52] U.S. Cl. ..................... 604/53; 604/280; 604/264; 604/164; 138/115
[58] Field of Search ........ 604/264, 280, 282, 271–275, 604/53, 52, 49, 164, 96, 102, 101, 93, 173, 258, 266, 268; 138/111, 118, 124, 115; 606/194

[56] References Cited

U.S. PATENT DOCUMENTS

| | | | |
|---|---|---|---|
| 3,888,249 | 6/1975 | Spencer | 604/280 |
| 4,299,226 | 11/1981 | Banka | 604/194 |
| 4,406,656 | 9/1983 | Hattler et al. | 604/96 |
| 4,717,379 | 1/1988 | Ekholmer | 604/280 |
| 4,748,984 | 6/1988 | Patel | 606/194 |
| 4,782,834 | 11/1978 | Maguire et al. | 604/280 |
| 4,795,439 | 1/1989 | Guest | 604/264 |
| 4,801,297 | 1/1989 | Mueller | 604/264 |

Primary Examiner—C. Fred Rosenbaum
Assistant Examiner—Kathleen A. Dally
Attorney, Agent, or Firm—Fulwider, Patton, Lee & Utecht

[57] ABSTRACT

A multilumen vascular catheter for the delivery of therapeutic fluids, e.g., containing thrombolytic agents, to a patient's blood vessel. The catheter has a plurality of flow passageways in the wall of the outer tubular member in which the discharge openings thereof increase in diametrical dimensions so that a desired, e.g., uniform, flow of treatment fluid is delivered exteriorly of the catheter body. The flow passageways preferably are formed by means of lasers. A first rectangularly shaped passageway is formed in the catheter wall and then a second rectangularly shaped hole is made in the wall, overlapping the first hole to form the final rectangular shape. The catheter is particularly adapted to deliver small quantities of thrombolytic agents, such as urokinase, streptokinase, and tissue plasminogen activator.

10 Claims, 1 Drawing Sheet

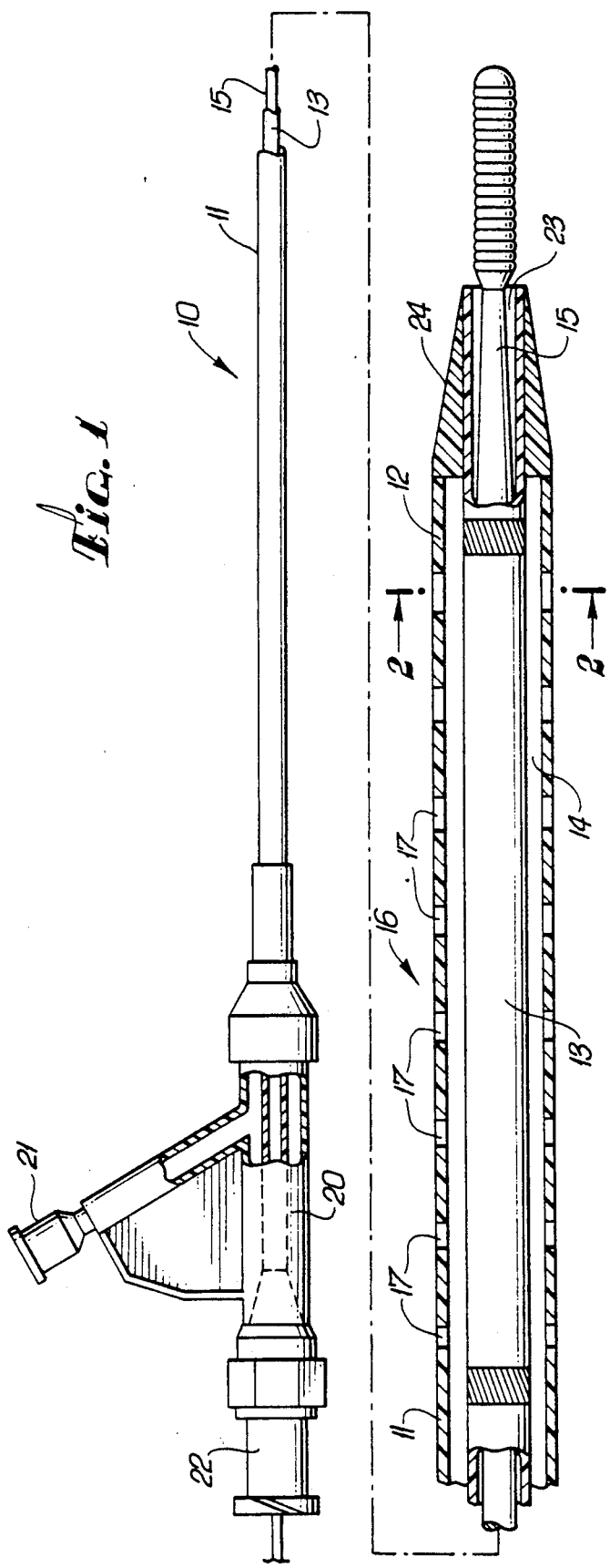
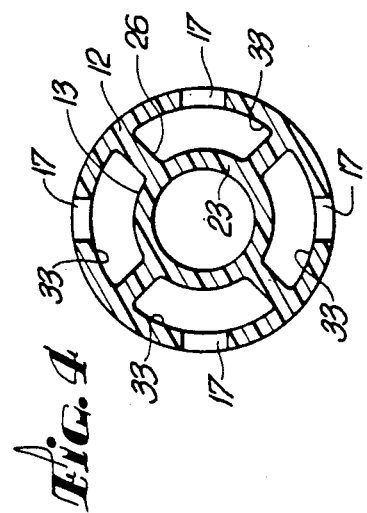
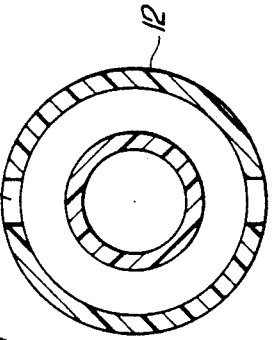
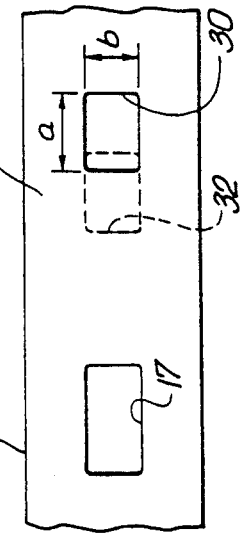

CATHETER FOR EVEN DISTRIBUTION OF THERAPEUTIC FLUIDS

BACKGROUND OF THE INVENTION

This invention generally relates to a vascular catheter for the delivery of therapeutic fluids and particularly for the uniform delivery of such fluids to an artery of a patient.

The utilization of therapeutic fluids such as those containing tissue plasminogin and activator (TPA), streptokinase, urokinase, and the like have been promising in the treatment of cardiovascular diseases. The systemic use of such therapeutic fluids has been limited by the fact that the total body is medicated in order to effect sites in the coronary anatomy. Delivery of such therapeutic fluids directly to the target tissue would allow a much more effective treatment procedure but to date, there have been no effective delivery systems, available. Moreover: there are no delivery systems which can deliver a uniform quantity of therapeutic fluids to a cardiovascular region, particularly at the low volume rates believed to be needed. The present invention provides such a system.

SUMMARY OF THE INVENTION

The present invention is directed to a vascular catheter which provides for a more effective uniform delivery of therapeutic fluids to a desired location within a patient's vasculature.

The vascular catheter in accordance with the present invention generally comprises an elongated tubular body having a first inner lumen for receiving a guidewire and at least one additional lumen for delivery of therapeutic fluids therethrough. A plurality of fluid flow passageways are provided through the outer wall of the tubular body to direct therapeutic fluids from within the one or more additional lumens to the exterior of the catheter to facilitate the delivery thereof to a specific site within the patient's vascular system. The passageways in the catheter wall generally are spaced longitudinally along a distal portion of the catheter and the discharge area per unit length thereof is progressively enlarged in the distal direction to maintain a desired flow pattern of therapeutic fluids to the treatment site. Preferably, the flow passageways in the tubular catheter wall are evenly spaced along a length of the catheter with the transverse cross-sectional area thereof increasing distally with successive passageways so as to provide a more uniform delivery of therapeutic fluids.

The presently preferred embodiment generally comprises an outer tubular member, an inner tubular member concentrically disposed within the outer tubular member and defining an annular lumen therebetween which is adapted to direct therapeutic fluids to the distal portion of the catheter having flow passageways in the wall thereof. The inner tubular member has a central lumen extending therethrough which is adapted to receive a guidewire so that the catheter can be advanced thereover to a desired location within the patient's vascular system. The flow passageways are preferably provided in a distal portion of the catheter and may be linearly or spirally disposed along the length depending upon the flow pattern desired at the vascular site. While in the presently preferred embodiment, the transverse cross-sectional area of evenly spaced flow passageways is increased in the distal direction to control the flow thereof, alternate embodiments would include an increase in the number of holes per unit of length or a decrease in the distal direction to increase the area of the discharge or variations in spacing.

The passageways in the catheter wall are preferably formed by a laser beam which can accurately form very small holes in the outer tubular member of the vascular catheter. Such small holes allow for the use of very low internal pressure within the annular lumen between the inner and outer tubular member which can be easily controlled to result in very low volume jets of fluid through each of such passageways onto the treatment site.

These and other advantages of the invention will become more apparent from the following detailed description of the invention, including the exemplary drawings.

BRIEF DESCRIPTION OF THE DRAWINGS

FIG. 1 is a elevational view partially in section of a vascular catheter for therapeutic fluids which embodies features of the invention;

FIG. 2 is a cross-sectional view taken along the lines of 2—2 shown in FIG. 1;

FIG. 3 is a top view taken along the lines of 3—3 shown in FIG. 1 to illustrate the size and placement of flow passageways in the distal operative portion of the catheter and;

FIG. 4 is an alternate embodiment of the present invention wherein multiple lumens are provided for delivery of treatment fluids.

DETAILED DESCRIPTION OF THE INVENTION

Reference is made to FIG. 1 which illustrates a vascular catheter assembly 10 which embodies features of the invention. In general the catheter assembly 10 includes an elongated tubular body 11 having an outer tubular member 12 and an inner tubular member 13 concentrically disposed within the outer tubular member and defining an annular lumen 14 therebetween. The inner tubular member 13 is adapted to receive a guidewire 15 which facilitates the advancement of the catheter assembly 10 to place the operative distal portion 16 thereof at a desired site in the patient's vascular system. The outer tubular member 12 is provided with a plurality of flow passageways 17 in the operative portion 16 which are spaced along the length thereof. The transverse cross-sectional area, i.e., the discharge area, of the passageways 17 increases with each successive passageway in the distal direction. The embodiment shown in FIG. 1 provides for the uniform spacing between the centerline of the individual passageways 17.

The proximal end of catheter assembly 10 is provided with a two-arm adapter 20, having one arm 21 for introducing therapeutic fluids into the annular lumen 14 and another arm for directing guidewire 15 into the lumen 23 within the inner tubular member 13.

A flexible tip 24 is provided on the distal end of tubular body 11 to lessen the trauma caused by the introduction of the catheter into the patient's blood vessel. Preferably, the tip is formed of a softer, more resilient plastic material than either the inner or outer member. As shown in FIG. 1, the inner tubular member 13 preferably extends to the distal tip of the tubular body 11 and supports the flexible tip 24. The flexible tip 24 closes off and seals the distal end of the annular lumen 14.

To provide a uniform flow of therapeutic fluids along the operative distal portion of the catheter 10, the discharge area of the flow passageways 17 per unit length of the operative portion 16 of the catheter increases in the distal direction. The transverse cross-section of individual passageways can be increased in the distal direction or in the alternative the number and density of passageways can be increased distally in order to maintain a desired uniform flow pattern of therapeutic fluid from the annular lumen 14.

In a presently preferred embodiment, the passageways 17 are formed through the outer tubular member 12 by means of a laser beam, preferably with a rectangular transverse cross section. The flow passageway is formed in two steps, as shown in FIG. 3. In the first step, an initial rectangular passageway 30 is formed by the laser beam through wall 31 of the outer tubular member 12 having a constant longitudinal dimension a with respect to the catheter axis (e.g., typically about 40 to about 80 microns) and a varying transverse direction b (e.g., typically from about 10 to about 60 microns). The discharge area for each hole generally should be less than 0.02 mm$^2$, preferably about 0.001 to about 0.01 mm$^2$. The second step involves the formation of an overlapping rectangularly shaped passageway 32 shown in phantom generally parallel to and axially in line with the first passageway 30 having essentially the same dimensions to produce an elongated rectangularly shaped passageway 17. Typical overlap is about 10 microns, which provides a typical longitudinal dimension of the finished flow passageway of about 70 microns. The spacing between the individual flow passageways 17 is about 1 to about 8 cm, preferably about 1 to about 4 cm from centerline to centerline. The presently preferred total number of flow passageways, as illustrated in FIG. 1, is 8 on one side of the outer tubular member 13. However, a greater or lesser amount of passageways can be employed and they need not be linearly spaced along one side. In the presently preferred embodiments, the flow passageways are drilled with a Model 1100 XMR laser device with an energy density of about 14 joules/cm.

The catheter components can be formed from conventional materials. For example, the outer tubular member 12 may be formed from extruded polyethylene with an outside diameter of 0.068 inch (1.72 mm) and an inside diameter of 0.058 inch (1.47 mm). The inner member may be formed from extruded polypropylene with an outside diameter of about 0.04 inch (1.02 mm) and an inside diameter of about 0.03 inch (0.76 mm). The multi-arm adapter 20 is generally formed of conventional polyethylene materials.

FIG. 4 illustrates an alternate embodiment where the outer tubular member 12 and inner tubular member 13 are formed (e.g., extruded) into a unitary structure with struts or walls 26 extending between the inner and outer tubular members forming a plurality of separated lumens 33. Each of the lumens may be provided with one or more flow passageways 17 as previously described.

To effectively remove thrombus, very low flow rates of about 0.1 to about 1.5 cm$^3$/hr have been found suitable. Such flow rates can be obtained with the present catheter assembly with internal fluid pressures of about 2 to about 5 psi.

The catheter assembly 10 of the invention is utilized by first passing a guidewire 15 through a thrombus in a patient's artery which is to be treated. The catheter 10 of the invention is then advanced over the guidewire into the thrombus so that the operative portion 16 of the catheter extends through the thrombus. Thrombolytic fluid, e.g., containing urokinase, streptokinase, TPA, or the like, is then pumped by suitable means such as a syringe mounted on arm 21 of adapter 20 through the annular passageway 14 at about 1 cm$^3$/hr. The slow delivery rates allow deep penetration of the thrombolytic fluid into the thrombus for the effective break-up and dissolution thereof. After the thrombus has been removed, the catheter 10 can then be removed over the guidewire 15. If an angioplasty is needed for atheroma underlying the thrombus, a conventional balloon dilatation catheter can then be advanced over the previously placed guidewire to the site of the atheroma for the dilation thereof.

While the present invention has been described herein in terms of certain preferred embodiments, various improvements can be made to the invention without departing from the scope thereof. For example, inflatable balloons can be provided on the distal and proximal ends of the operative portion of the catheter in order to occlude the patient's blood vessel, thereby holding the thrombolytic or other treatment fluid within the desired region of the patient's blood vessel. Other modifications can be made to the invention.

What is claimed is:

1. A multilumen catheter having an operative distal portion for the uniform delivery of therapeutic fluid to a location within a patient's vascular system, comprising:

a) an elongated tubular body having proximal and distal ends, a first longitudinally extending inner lumen with an axial opening in the distal end of the tubular body which is adapted to receive a guidewire and a sidewall which defines at least in part an additional longitudinally extending inner lumen adapted to receive therapeutic fluid;

b) a plurality of longitudinally spaced fluid passageways which extend radially through the sidewall of the elongated tubular body in the operative distal portion of the catheter from the additional inner lumen to the exterior of the tubular body and which are adapted to direct therapeutic fluid from the additional inner lumen to the exterior of the tubular body, the transverse cross-sectional area of the passageways and the spacing therebetween being controlled to provide a flow discharge area per unit length of the operative distal portion of the catheter which increases in the distal direction to provide a uniform flow of therapeutic fluid to the exterior of the tubular member; and c) means at the proximal end of the tubular member to direct treatment fluid to the additional lumen adapted to receive said fluid.

2. The catheter of claim 1 wherein the elongated tubular body comprises an inner tubular member having he first lumen disposed longitudinally therein and an outer tubular member disposed concentrically about the inner tubular member and defining an annular additional lumen between the inner and outer tubular members.

3. The catheter of claim 2 wherein the annular additional lumen adapted to receive therapeutic fluid is divided into separate parallel lumens by wells which extend between the inner and outer tubular members.

4. The catheter of claim 1 wherein the flow passageways through the wall of the tubular body are equally spaced in the longitudinal direction.

5. The catheter of claim 1 wherein the flow passageways have transverse cross-sectional areas less than 0.02 mm$^2$.

6. The catheter of claim 1 wherein the flow passageways have transverse cross-sectional areas of about 0.001 to about 0.01 mm$^2$.

7. The catheter of claim 1 wherein the transverse cross-sectional shape of the flow passageways is rectangular.

8. The catheter of claim 1 wherein the flow passageways through the wall of the tubular body are evenly spaced longitudinally therein.

9. A method for treating a thrombus in a region of a patients s blood vessel comprising:
  a) advancing a guidewire through the region of the patient's blood vessel having a thrombus;
  b) advancing a multilumen catheter over the guidewire until an operative distal portion of the catheter extends into the region having the thrombus, the catheter comprising:
    an elongated tubular body having proximal and distal ends, a first lumen with an axial opening in the distal end of the tubular body which receives the guidewire and a wall which defines at least in part an additional inner lumen which receives thrombolytic fluid at the proximal end thereof;
    a plurality of radially extending, longitudinally spaced fluid passageways in the operative distal portion of the catheter which extend through the sidewall of the elongated tubular body from the inner lumen, said passageways having
    a transverse cross-sectional area increasing in the distal direction so that there is uniform flow of thrombolytic fluid from the additional inner lumen to the exterior of the tubular body along the operative distal portion of the catheter; and
  b) directing thrombolytic fluid through the additional inner lumen to discharge such fluid through the radially extending passageways in a uniform manner into thrombus surrounding the operative portion of the catheter along the length thereof.

10. The method of claim 9 wherein the multilumen catheter is withdrawn over the guidewire and a balloon dilatation catheter is advanced over the guidewire so the balloon thereon crosses the lesion in the patient's blood vessel which underlies the thrombus inflating the balloon with inflation fluid at elevated pressure to dilate the lesion and then deflating the balloon so the catheter can be withdrawn from the patient's blood vessel.

* * * * *